United States Patent
Vujaskovic et al.

(10) Patent No.: US 9,415,065 B2
(45) Date of Patent: Aug. 16, 2016

(54) METHODS OF USING CERIUM OXIDE NANOPARTICLES TO MITIGATE OR PROTECT AGAINST RADIATION INJURY

(71) Applicants: DUKE UNIVERSITY, Durham, NC (US); UNIVERSITY OF CENTRAL FLORIDA RESEARCH FOUNDATION, INC., Orlando, FL (US)

(72) Inventors: Zeljko Vujaskovic, Chapel Hill, NC (US); Isabel L. Jackson, Baltimore, MD (US); Sudipta Seal, Oviedo, FL (US); Soumen Das, Orlando, FL (US)

(73) Assignees: UNIVERSITY OF CENTRAL FLORIDA RESEARCH FOUNDATION, INC., Orlando, FL (US); DUKE UNIVERSITY, Durham, NC (US)

(*) Notice: Subject to any disclaimer, the term of this patent is extended or adjusted under 35 U.S.C. 154(b) by 0 days.

(21) Appl. No.: 14/390,517

(22) PCT Filed: Mar. 13, 2013

(86) PCT No.: PCT/US2013/030811
§ 371 (c)(1),
(2) Date: Oct. 3, 2014

(87) PCT Pub. No.: WO2013/151698
PCT Pub. Date: Oct. 10, 2013

(65) Prior Publication Data
US 2015/0056283 A1    Feb. 26, 2015

Related U.S. Application Data (60) Provisional application No. 61/620,219, filed on Apr. 4, 2012.

(51) Int. Cl.
*A61K 33/24* (2006.01)
*A61K 9/51* (2006.01)

(52) U.S. Cl.
CPC .. *A61K 33/24* (2013.01); *A61K 9/51* (2013.01)

(58) Field of Classification Search
CPC .................................. A61K 33/24; A61K 9/51
See application file for complete search history.

(56) References Cited

U.S. PATENT DOCUMENTS

| | | | |
|---|---|---|---|
| 7,141,227 B2 | 11/2006 | Chan | |
| 7,186,700 B2 * | 3/2007 | Standring | A61K 31/7068 514/42 |
| 7,347,987 B2 | 3/2008 | McGinnis et al. | |
| 7,431,758 B2 | 10/2008 | Ota et al. | |
| 7,504,356 B1 | 3/2009 | Self et al. | |
| 7,534,453 B1 | 5/2009 | Rzigalinski et al. | |
| 7,727,559 B2 | 6/2010 | McGinnis et al. | |
| 8,097,270 B2 | 1/2012 | Ketelson et al. | |
| 8,337,898 B2 | 12/2012 | Seal et al. | |
| 8,703,200 B2 | 4/2014 | McGinnis et al. | |
| 8,795,737 B2 | 8/2014 | Seal et al. | |
| 8,916,199 B1 | 12/2014 | Seal et al. | |
| 2004/0009349 A1 | 1/2004 | Brotzman et al. | |
| 2005/0066571 A1 | 3/2005 | Wakefield | |
| 2007/0072825 A1 | 3/2007 | Williams | |
| 2009/0097336 A1 | 4/2009 | Kang et al. | |
| 2010/0166821 A1* | 7/2010 | Rzigalinski | A61K 9/14 424/423 |
| 2010/0242342 A1 | 9/2010 | Reed et al. | |

FOREIGN PATENT DOCUMENTS

| | | |
|---|---|---|
| JP | 2007-22836 | 2/2007 |
| JP | 2007022836 A * | 2/2007 |
| WO | WO 03/059263 | 7/2003 |
| WO | WO 2006/118954 | 11/2006 |
| WO | WO 2007/002662 | 1/2007 |
| WO | WO 2008/064357 | 5/2008 |
| WO | WO 2009/132277 | 10/2009 |

OTHER PUBLICATIONS

Colon, J. et al. "Cerium oxide nanoparticles protect gastrointestinal epithelium from radiation-induced damage by reduction of reactive oxygen species and upregulation of superoxide dismutase 2", Nanomedicine: NBM 2010;6:698-705.*

Tarnuzzer, R. et al. "Vacancy engineered ceria nanostrctures for protection from radiation-induced cellular damage", Nano Letters, 2005, vol. 5, No. 12, 2573-2577.*

Sokolov, K. et al. "Real-Time Vital Optical Imaging of Precancer Using Anti-Epidermal Growth Factor Receptor Antibodies Conjugated to Gold Nanoparticles." Cancer Res. 63: 1999-2004 (2003).

Suh, W. H. et al. "Multifunctional nanosystems at the interface of physical and life sciences." Physicaplus Online Magazine of the Israel Physical Society (IPS), 13 (2010).

Suzuki, M. et al. "Preparation and characteristics of magnetite-Labelled antibody with the use of poly(ethylene glycol) derivatives." Bitotechnology Applied Biochemisty, 21: 335-345 (1995).

Tarnuzzer et al, "Vacancy Engineered Ceria Nanostructures for Protection from Radiation-Induced Cellular Damage", Nano Letters 5(12):2573-2577 (2005).

Tsai, Ming-Shyong. "The Study of the synthesis of nano-grade cerium oxide powder," Materials Letters 58, 2270-2274 (2004)****.

(Continued)

*Primary Examiner* — Gina Justice
(74) *Attorney, Agent, or Firm* — Andrus Intellectual Property Law, LLP (57) ABSTRACT

Methods of mitigating the effects of radiation exposure or providing a radioprotective effect in a subject are provided herein. The methods include administering a therapeutically effective amount of cerium oxide nanoparticles to the subject to mitigate the effects of radiation exposure or to offer a radioprotective effect to the subject. The cerium oxide nanoparticles are suitably less than 20 nm in diameter and have over 50% of the cerium in the 3+ oxidation state.

20 Claims, 4 Drawing Sheets

(56) References Cited

OTHER PUBLICATIONS

Tusnekawa, S., et al. "Lattice relaxation of monosize Ce02-x nanocrystalline particles" Applied Surface Science Elsevier Netherlands, vol. 152, No. 1-2, Nov. 1999, pp. 53-56, XP002491212 ISSN: 0169-4332 * p. 53, col. 1, paragraph 2—col. 2, paragraph 1 ****.
Vujaskovic et al, "Cerium Oxide Nanoparticles Protect Lung From Radiation-induced Injury in CBA/J Mice", Proceedings of the American Society for Radiation Oncology 54th Annual Meeting Supplement 84(3):S683 (2012).
Xijuan, et al. "Size-dependent optical properties of nanocrystalline Ce02:Er obtained by combustion synthesis," Sep. 24, 2001, Phys. Chem. Chem Phys., vol. 3, pp. 5266-5269 ****.
Zhang, et al. Cerium oxide nanoparticles: size selective formation and structure analysis, Jan. 7, 2002, Applied Physics Letters, vol. 81, No. 1, p. 127-129****.
Office Action for U.S. Appl. No. 12/772,523 mailed Sep. 15, 2011.
International Search Report for PCT/US2011/044329 mailed Dec. 8, 2011.
Bailey, D., et al. "Cerium Oxide Nanoparticles Extend Cell Longevity and Act as Free Radical Scavengers," online [retreived on Apr. 24, 2006 retrieved from: http://wwww.med.miami.edu.mnbws/Rzigalinski11,.html].
Baker, Ch, "Radiation protection with nanoparticles", Nanomedicine in Health and Disease, pp. 268-292 (2011).
Bakht et al, "A novel technique for simultaneous diagnosis and radioprotection by radioactive cerium oxide nanoparticles: study of cyclotron production of 137mCe", Journal of Radioanalytical and Nuclear Chemistry 292(1):53-59 (2011).
Birch, D.G. et al. "Age-related macular degeneration: a target for nanotechnology derived medicines", International Journal of Nanomedicine 2(1): 65-77 (2007).
Chen, et al. "Rare Earth Nanoparticles Prevent Retinal Degeneration Induced by Intracellular Peroxides." Nature Nanotechnology, 1(2) 142-148 (2006).
Colon et al, "Protection from radiation-induced pneumonitis using cerium oxide nanoparticles", Nanomedicine: Nanotechnology, Biology and Medicine 5(2):225-231 (2009).
Colon et al, "Cerium oxide nanoparticles protect gastrointestinal epithelium from radiation-induced damage by reduction of reactive oxygen species and upregulation of superoxie dismutase 2", Nanomedicine: Nanotechnology, Biology and Medicine 6(5):698-705 (2010).
Cook, et al. "Neuronal Damage induced by polychlorinated biphenyls is partially reversed by cerium oxide nanoparticles" [online] vol. 2003, 2003, XP008095032 Retrieved from the internet: URL http://sfn.scholarone.com/itin2003/main.htm]?new_page_id=126&abstract_id=14513&p_num=669.13&is_tech=0> [retrieved on Aug. 5, 2008] *abstract*.
Devasenapathi, A. et al. "Forming near net shape free-standing components by plasma spraying." Materials Letters 57: 882-886 (2002).
Dong, S. et al. "Activation of Glassy Carbon Electrodes by Dispersed Metal Oxide Particles." J. Electrochem Soc., 813-813 (1984).
Eck, W. et al. "PEGylated Gold Nanoparticles Conjugated to Monoclonal F19 Antibodies as Targeted Labeling Agents for Humann Pancreatic Carcinoma Tissue." ACS Nano, 2(11): 2263-2272 (2008).
Guo. "Green and red upconversion luminescence in Ce02:Er3+ powders produced by 785 nm laser," Oct. 10, 2006, Jounral of Solid State Chemistry 180, p. 127 ****.
Hahn, P. et al. "Maculas Affected by Age-Related Macular Degeneration Contain Increased Chelatable Iron in the Retinal Pigment Epithelium and Bruch's Membrane." Arch Ophthalomol, vol. 121 (Aug. 2003).
Haywood, L. et al. "Inflammation and Angiogenesis in Osteoarthritis." Arthritis & Rheumatism, 48(8): 2173-2177 (2003).
Hollyfield, J.G. et al. "Oxidative damage-induced inflammation initiates age-reltated macular degeneration." Nature Medicine, 14(2): 194-198 (2008).
Hooper, C.Y. et al. "New treatments in age-related macular degeneration." Clinical and Experimental Ophthalmology, 31: 376-391 (2003).
Imamura, Y. et al. "Drusen, choroidal neovascularization, and retinal pigment epithelium dysfunction in SOD1-deficient mice: A model of age-related macular degeneration." PNAS, 103(30): 11282-11287 (2006).
Jin, S. et al. "Nanoparticle-Mediated Drug Delivery and Gene Therapy." Biotechnol. Prog. 23:32-41 (2007).
Karakoti, et al. "Direct Synthesis of Nanoceria in Aqueous Polyhydroxyl Solutions." J. Phys. Chem. C, 111: 17232-17240 (2007).
Karakoti et al, "Nanoceria as Antioxidant: Synthesis and Biomedical Applications", JOM 60(3):33-37 (2008).
Liu, Y. et al. "Subtype lesions of neovascular age-related macular degeneration in Chinese patients." Graefe's Arch Clin Exp Ophthalmol. 245: 1441-1445 (2007).
Madero-visbal et al, "Harnessing nanoparticles to improve toxicity after head and neck radiation", Nanomedicine: Nanotechnology, Biology and Medicine, 8(7):1223-1231 (2012).
Margrain, T. H. et al. "Do blue light filters confer protection against age-related macular degeneration?" Progress in Retinal and Eye Research, 23(5): 523-531 (2004).
Maschio, R. D. et al. "Influence of $Ce^{3+}/Ce^{4+}$ ratio on phase stability and residual stress field in ceria-yttria stabilized zirconia plasma-sprayed coatings." Journal of Materials Science, 27: 5591-5596 (1992).
Maulik, N. "Reactive Oxygen Species Drives Myocardial Angiogenesis?" Antioxidants & Redox Signaling, 8(11 & 12): 2161-2168 (2006).
Monte, M. et al. "Inhibition of lymphocyte-induced angiogenesis by free radical scavengers." Free Radic Biol Med. 17(3): 259-66 (1994).
Moongkarndi, P. et al. "Antiproliferation, antioxidation and induction of apoptosis by *Garcinia* mangostana (mangosteen) on SKBR3 human breast cancer cell line." Journal of Ethnopharmacology, 90: 161-166 (2004).
Nafee "Dissertation entitled Cationically-modified nanoparticles for the pulmonary delivery of-the telomerase inhibitor 2'-O.Methyl RNA for the treatment of lung cancer." Dissertation zur Erlangung des Grades des Doktors der Naturwissenschaften der Naturwissenschaftlich-Technischen Fakult't III Chemie' Pharmazie, Bio-Und Werkstoffwissenschaften Der Universt Des Saarlandes (2008).
Nazem, A. et al. "Nanotechnology for Alzheimer's disease detection and treatment." Insciences J. 1(4): 169-193 (2011).
Niu, J., et al. "Cardioprotective effects of cerium oxide nanoparticles in a transgenic murine model of cardiomyopathy," Cardiovas. Res. Nov. 30, 2006, vol. 73, No. 3, pp. 549-559.
Ohgushi, H. et al. "Stem Cell Technology and Bioceramics: From Cell to Gene Engineering." J Biomed Mater Res. 48(6): 913-27 (1999).
Ohia, S. E. et al. "Pharmacological consequences of oxidative stress in ocular tissues." Mutation Research, 579: 22-36 (2005).
Olivier, J. et al. "Synthesis of Pegylated Immunonanoparticles." Pharmaceutical Research, 19(8): 1137-1143 (2002).
Otsuka, H. et al. "PEGylated nanoparticles for biological and pharmaceutical applications." Advanced Drug Delivery Reviews, 55: 403-419 (2003).
Patil, et al. "Synthesis of nanocrystalline ceria particles for high temperature oxidation resistant coating," Journal of Nanoparticle Research, 2002, vol. 4: pp. 433-438 ****.
Patil, S. et al. "Surface-Derivatized Nanoceria with Human Carboni Anhydrase II Inhibitors and Fluorophores: A Potential Drug Delivery Device." J. Phys. Chem. C 11: 8437-8442 (2007).
Perez, J. M., et al. "Synthesis of Biocompatible Dextran-Coated Nanoceria with pH-Dependent Antioxidant Properties," Small, vol. 4 No. 5, 2008, pp. 552-556, published online Apr. 24, 2008 ****.
Qi, et al. "Redispersible Hybrid Nanopowders; Cerium Oxide Nanoparticle complexes with Phosphonated-PEG Oligomers," ACS Nano, 2008, vol. 2(5), pp. 879-888. ****.
Qureshi, M. A. et al. "Increased Exhaled Nitric Oxide Following Autologous Peripheral Hematopoietic Stem-Cell Transplantation: A Potential Marker of Idiopathic Pneumonia Syndrome." Chest, 125: 281-287 (2004).

(56) References Cited

OTHER PUBLICATIONS

Ramsfjell, V. et al. "Distinct Requirements for Optimal Growth and In Vitro Expansion of Human $CD34^+CD38^-$ Bone Marrow Long-Term Culture-Initiating Cells (LTC-IC), Extended LTC-IC, and Murine In Vivo Long-Term Reconstituting Stem Cells." Blood, 94(12): 4093-4102 (1999).

Rzigalinski, et al. "Cerium Oxide nanoparticles increase the lifespan of cultured brain cells and protect against free radical and mechanical trauma," FASEB Journal 17(4-5), Abstract No. 3377.24, Mar. 2003, p. A606.

Safi et al, "Interactions between sub-10-nm iron and cerium oxide nanoparticles and 3T3 fibroblasts: the role of the coating and aggregation state", Nanotechnology 21(14):145103 (2010).

Schubert, et al. "Cerium and yttrium oxide nanoparticles are neuroprotective," Feb. 3, 2006, Biochemical and Biophysical Research Communications, 342: 86-91.

Shui, Y. et al. "Morphological Observation on Cell Death and Phagocytosis Induced by Ultraviolet Irradiation in a Cultured Human Lens Epithelial Cell Line." Exp. Eye Res. 71: 609-618 (2000).

Sigma Catalog (2004).

Silva. G. "Seeing the benefits of ceria." Nature Nanotechnology, 1: 92-94 (2006).

Heckert, E.G. et al., "The role of cerium redox state in the SOD mimetic activity of nanoceria," (2008) Biomaterials 29:2705-2709.

Pirmohamed, T. et al., "Nanoceria exhibit redox state-dependent catalase mimetic activity," (2010) Chem. Comm. 46:2736-2738.

* cited by examiner

Figure 3:
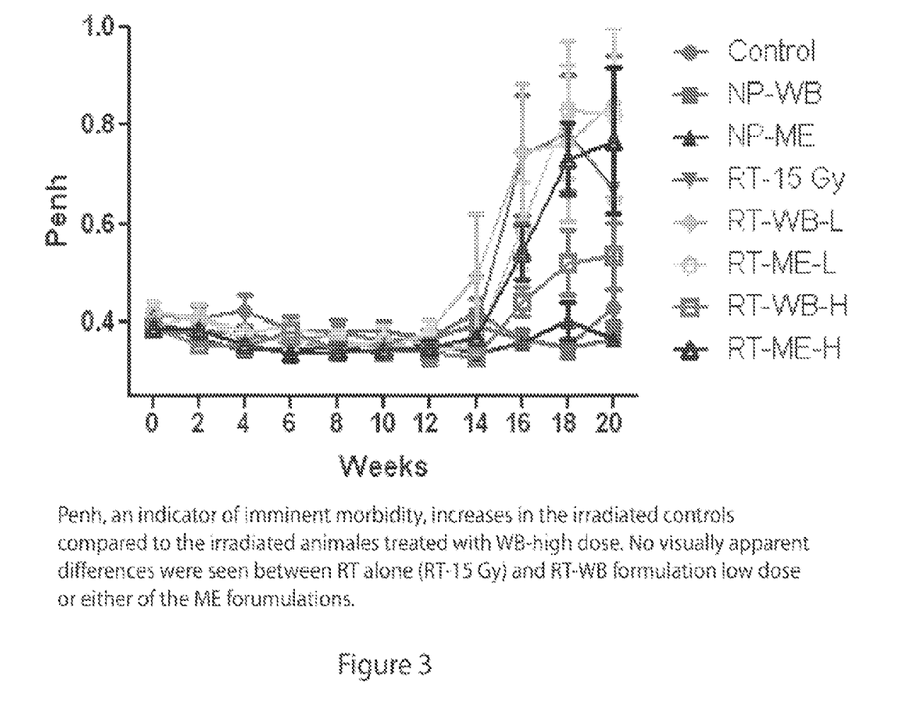
FIG. 3 is a graph showing the Penh levels (an indicator of imminent morbidity over time in mice treated with the indicated treatments two hours after irradiation.

Penh, an indicator of imminent morbidity, increases in the irradiated controls compared to the irradiated animales treated with WB-high dose. No visually apparent differences were seen between RT alone (RT-15 Gy) and RT-WB formulation low dose or either of the ME forumulations.

HRTEM image of nanoceria shows nanoparticles size range of 3-5nm (1A). (1B) is the high magnification image of nanoparticle and SEAD pattern represents the fluorite crystal structure in the inset where A, B, C and D corresponds to different lattice pattern 111, 200, 220 and 311, respectively. (1C) represents the hydrodynamic radius of the nanoparticle in the size range <10nm. (1D) Bar-diagram represents the cell viability/proliferation at different concentration of nanoceria and vehicle control, no cytotoxicity were observed at selected concentration range of nanoceria.

Figure 6

METHODS OF USING CERIUM OXIDE NANOPARTICLES TO MITIGATE OR PROTECT AGAINST RADIATION INJURY

CROSS-REFERENCE TO RELATED APPLICATIONS

This patent application is a national stage filing under 35 U.S.C. 371 of International Application No. PCT/US2013/030811, filed Mar. 13, 2013, which claims the benefit of priority of U.S. Provisional Patent Application No. 61/620,219, filed Apr. 4, 2012, both of which are incorporated herein by reference in their entirety.

STATEMENT REGARDING FEDERALLY SPONSORED RESEARCH

This invention was made with United States government support awarded by the National Institutes of Health grant number 1RC1AIO81290-01. The United States may have certain rights in this invention.

INTRODUCTION

The present invention relates to the field of nanotechnology and in particular to ceria nanoparticles and methods of using the same to mitigate the effects of radiation.

Nanotechnology is rapidly emerging as an important tool in the field of medicine. Among various nanoparticles, cerium oxide nanoparticles have a unique regenerative antioxidant property and can efficiently scavenge reactive oxygen/nitrogen species species ($H_2O_2$, $O_2$, $OH^-$ and $^-NO$). One of the cerium oxide nanoparticle ($CeO_2$; CNP) formulations, CNP-18, was reported well-tolerated, non-immunogenic and without overt pathology in small animal in vivo models.

Lung injury is the major cause of death following acute radiation exposure to the thoracic region. Anecdotal evidence described in the literature suggests radiation accident victims receiving a whole body dose in excess of 10 Gy may experience partial hematological recovery with excellent supportive care. However, in these individuals death due to acute respiratory distress occurred three to six months after exposure due to radiation induced lung injury. At the time of death, the lungs were congested and edemic suggestive of interstitial pneumonia with diffuse alveolar damage and in some cases, fibrous lesions were present. There is no FDA approved medical countermeasure (MCM) to mitigate lung damage and improve survival following acute radiation exposure.

SUMMARY

Provided herein are methods of improving survival and mitigating the damage, in particular lung damage, caused by acute radiation exposure. In particular, methods of mitigating the effects of radiation exposure in subjects exposed to radiation are provided. The methods include administering as composition comprising cerium oxide nanoparticles (CNPs) to the subject in an amount effective to mitigate the effects of radiation exposure. In particular, the methods mitigate the lung damaging effects of radiation even when the composition is provided after radiation exposure.

DETAILED DESCRIPTION

Since Sep. 11, 2001, the U.S. government has placed increasing emphasis on developing and stockpiling medical countermeasures (MCMs) to treat acute radiation syndrome (ARS) in the event of a nuclear or radiological attack on U.S. soil. At this time there is no approved MCM for treating the delayed effects of acute radiation exposure, specifically acute and delayed lung injury (DEARE-lung). One of the primary concerns associated with thoracic irradiation is an acute but delayed onset of radiation pneumonitis with an incidence that rises very steeply at relatively low radiation doses. Previous studies indicate that the initial oxidative stress produced during the radiation event is amplified through continuous production of reactive oxygen/nitrogen species (ROS/RNS) leading to an Unbalance between oxygen derived free radicals and antioxidant capacity. The continuous generation of ROS plays a central role in the underlying processes of radiation injury through activation/de-activation of key redox-regulated signaling pathways leading to acute pneumonitis as an early event and/or chronic fibrosis as a late event. Antioxidant therapies may be useful to reduce inflammation and fibrosis in rodent models of radiation-induced lung injury. Therefore, we hypothesized that the potent antioxidant properties of specially designed nanoceria may improve survival after radiation injury by restoring the redox balance of the cell.

In the Examples, we demonstrate mitigation of lung injury and improvement in survival after treatment with 100 nM CNP-18 starting 2 hours after acute radiation exposure to the thorax. Thus nanoceria are capable of improving survival and reducing lung damage when provided to subjects after irradiation. Thus, methods of mitigating the effects of radiation exposure in subjects exposed to radiation are provided. The methods include administering a composition comprising GNPs to the subject in an amount effective to mitigate the effects of radiation exposure. In particular, the methods mitigate the lung damaging effects of radiation even when the composition is provided after radiation exposure. The CNPs were made and characterized using methods described more fully in the Examples.

The radiation exposure level used in the Examples was a 90% lethal dose over 160 days. Lower or sub-lethal doses of radiation also cause similar effects on subjects and may lead to decreased lung performance or increased lung damage after exposure which may be mitigated by treatment with the cerium oxide nanoparticles as described herein. Mitigating the effects of radiation includes, but is not limited to, improving survival after radiation exposure, reducing morbidity, reducing lung damage, improving respiratory or lung functions, which may be measured by monitoring the respiratory function of the subject, for example, by monitoring the breathing frequency, enhanced pause (Penh), tidal volume (TV), peak respiratory flow (PIF), peak expiratory flow (PEF), and inflammation in the lungs. Treating a subject as used herein refers to any type of treatment that imparts a benefit to the subject, including improvement in the condition of the subject (e.g., in one or more symptoms), delay in the progression of the condition, delay the onset of symptoms or slowing the progression of symptoms, etc.

Although some compositions have been demonstrated to otter radioprotection if given to the subject prior to radiation exposure, compositions capable of mitigating the effects of radiation exposure when administered after the exposure are not available. The compositions provided herein are capable of mitigating the effects of radiation exposure when administered at the same time as or after radiation exposure. This surprising effect is demonstrated in the Examples in a mouse model. The composition comprising; cerium oxide nanoparticles may be administered 1 hour, 2 hours, 4 hours, 6 hours, 8 hours, 12 hours, 24 hours, 2 days, 3 days, 4 days, 5 days, 6 days or even 1 or 2 weeks after exposure to the radiation. The composition may be administered multiple times at intervals of 1 day, 2 days, 3 days, bi weekly, weekly, bimonthly or monthly.

An effective amount or a therapeutically effective amount as used herein means the amount of the composition that, when administered to a subject for treating radiation exposure is sufficient to alert a treatment (as defined above). The therapeutically effective amount will vary depending on the formation of the composition, formulation or combination, the severity and timing of exposure to radiation and the age, weight, physical condition and responsiveness of the subject to be treated. Subjects include mammals, such as humans, mice, rats, dogs, cats, cows, pigs and non-mammals such as chickens, turkeys or other animals.

In the Examples, the cerium oxide nanoparticles were demonstrated to protect 90% of the mice when given two times a week for four weeks at 7 µg/kg commencing two hours after exposure to a 90% lethal dose of radiation. Thus in the Examples, the nanoceria was capable of increasing survival by 80%. Suitably, the methods described herein are capable of increasing the survival chance of a subject after exposure to radiation by at least 30%, 35%, 40%, 45%, 50%, 55%, 60%, 65%, 70%, 75%, 80%, 85%, 90% or even more.

Figure 1:
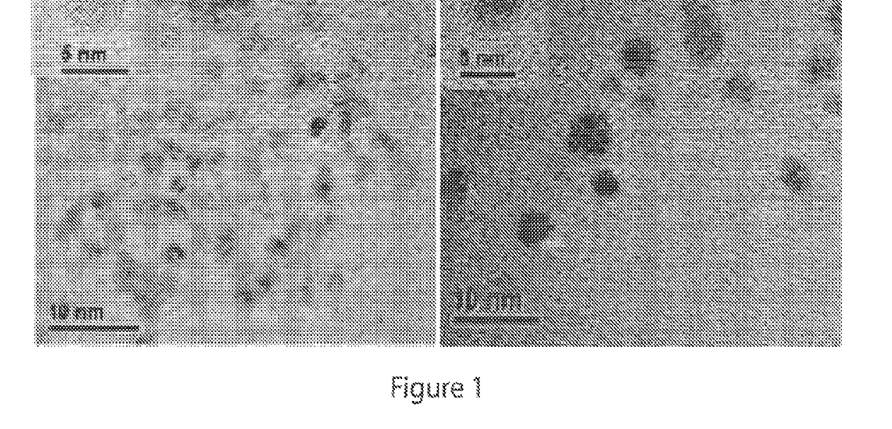
FIG. 1 is a set of photographs of transmission electron micrographs of the nanoceria particles when made in water (referred to as CNP-18 or CNP-WB) and polyethylene glycol (also referred to as CNP-300 or CNP-ME).
Figure 6:
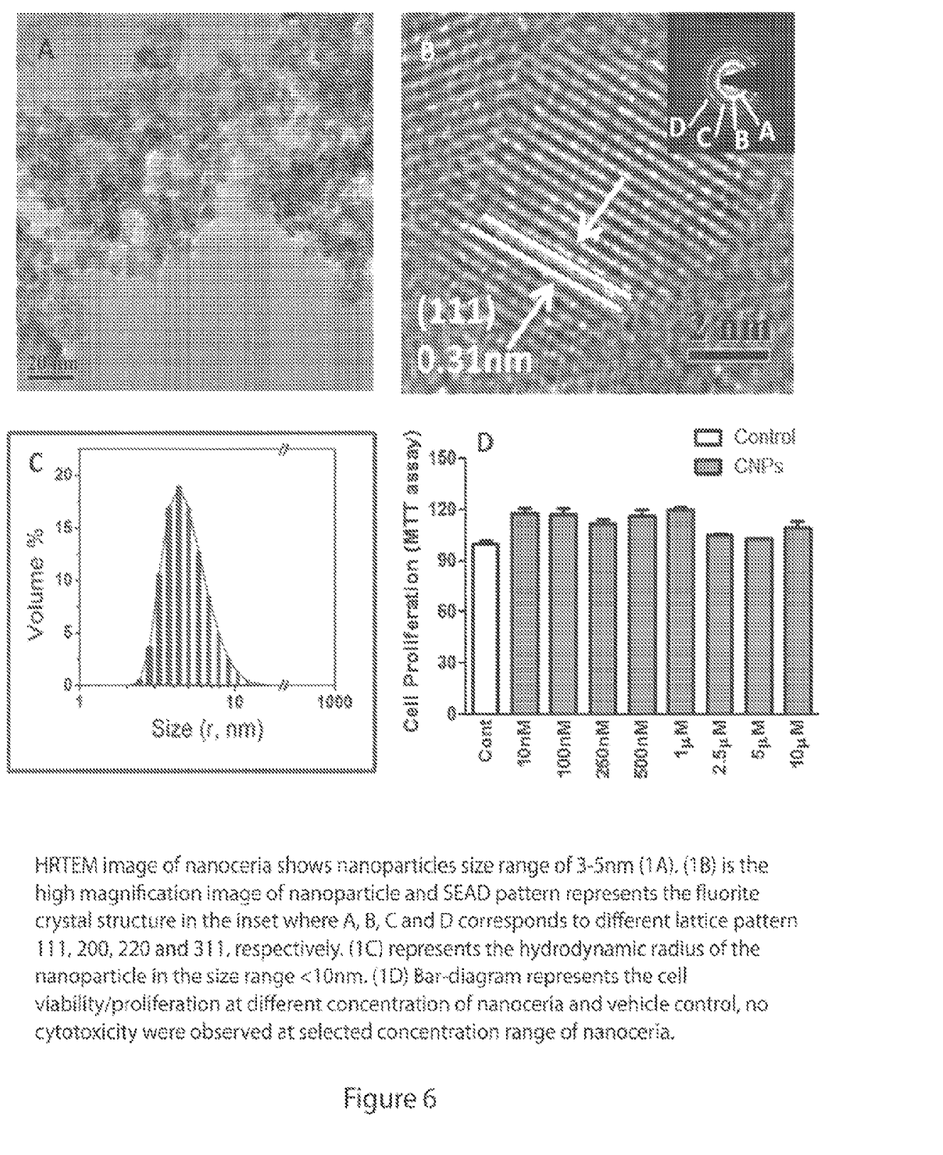
FIG. 6A is a photograph of a transmission electron micrograph showing the nanoparticles.
FIG. 6B is a photograph of a high magnification image of a nanoparticle showing the structure.
FIG. 6C is a graph showing the size range of the nanoparticles used.
FIG. 6D is a graph showing the results of as MTT cell viability assay after the cells were incubated with the indicated, concentrations of CNP-18 for 24 hours. No cytotoxicity was observed.

The compositions comprising cerium oxide nanoparticles may be made by methods known to those of skill in the art. See, for example, U.S. Pat. Nos. 7,347,987 and 7,727,559; U.S. patent application Ser. No. 12/874,398, entitled Polycrystalline Nanoparticles of Cerium Oxide and Associated Methods; and Karakoti et al. Nanoceria as Antioxidant: Synthesis and Biomedical Applications JOM (2008) 60:33-37 for methods of preparing cerium oxide nanoparticles, each of which are incorporated herein by reference in their entireties. Suitably the cerium oxide nanoparticles have particle diameters that are between 1 nm and 20 nm, suitably between 1 nm and 10 nm, suitably between 1 nm and 3 nm. Transmission electron micrographs of the nanoparticles are shown in FIGS. 1 and 6A and B. FIG. 6C shows the size distribution of the nanoparticles.

Suitably the cerium oxide nanoparticles are prepared such that more than 50% of the cerium in the nanoparticles is in the 3+ oxidation state. Suitably, at least 50%, 55%, 60%, 65%, 70%, 75%, 80%, 85% 90% or even more of the nanoparticles in the composition are in the 3+ oxidation state in the composition. The nanoparticles may be prepared in water or short polar solvents compatible with biological systems. The cerium oxide nanoparticles may complexed or coated with a biologically compatible polymer or polysaccharide such as polyethylene glycol or dextran. In the Examples, the nanoparticles were prepared in water or as a microemulsion. The nanoparticles prepared in water were shown to be more effective than those prepared as a microemulsion in our preliminary experiments shown in the Examples. The compositions may also comprise other pharmaceuticals useful in mitigating the effects of radiation exposure such as other pharmaceuticals such as antioxidants or may also include pharmaceutically acceptable additives or excipients.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal. In the Examples, the CNP were provided via intraperitoneal injection. Thus the compositions may be formulated as an ingestable, injectable, or topical formulation or for delivery via an osmotic pump. The compositions could also be provided as an aerosol formulation for direct delivery to the lung via inhalation. The compositions may also be delivered within a liposomal or time-release vehicle. Administration of the compositions to a subject in accordance with the invention appears to exhibit beneficial effects in a dose-dependent manner. Thus, within broad limits, administration of larger quantities of the compounds is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions being administered, the formulation of the composition, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages liar a given patient can be determined using conventional considerations, e.g., by customary comparison of the differential activities of the compositions and of a known agent, such as by means of an appropriate conventional pharmacological or prophylactic protocol.

The maximal dosage for a subject is the highest dosage that does not cause undesirable or intolerable side effects. As shown in FIG. 6D, no toxicity is detected in vitro at any of the doses tested up to 10 µM. In the Examples, a 100 nM dose of CNP-18 was effective to significantly reduce both morbidity and mortality after a lethal dose of radiation was administered. The number of variables in regard to an individual prophylactic or treatment regimen is large, and a considerable range of doses is expected. The route of administration will also impact the dosage requirements. It is anticipated that dosages of the composition will reduce morbidity and/or mortality by at least 10%, 20%, 30%, 40%, 50%, 60%, 70%, 80%, 90% or 100% compared to morbidity or mortality if the radiation exposure is left untreated. It is specifically contemplated that pharmaceutical preparations and compositions may palliate or alleviate symptoms of radiation exposure without providing a cure, or, in some embodiments, may be used to reverse the effects of radiation exposure.

The cerium oxide nanoparticles may be administered at a dosage between about 0.00005 mg/kg and 0.5 mg/kg. Suitably, the dosage is between about 0.005 mg/kg and 0.05 mg/kg. In the examples, the dosages used were between about 0.00007 mg/kg and 0.007 mg/kg. The composition may be formulated such that the cerium oxide nanoparticles are between 10 nM and 10 µM. Suitably, the cerium oxide nanoparticles are present at between 100 nM and 1 µM in the composition.

The compositions may be administered as a single dose or as multiple doses. Suitable effective total dosage amounts for administering the compositions may be determined by those of skill in the art, but typically range from about 50 nanograms to about 1 milligram per kilogram of body weight, although they are typically about 1-100 micrograms per kilogram of body weight. The dosage used in the Examples and shown to be effective was about 56 µg/kg given in 8 doses of 7 µg/kg in each dose. Large doses may be required for therapeutic effect and toxicity of the composition is low. In some embodiments, the effective dosage amount ranges from about 1 to about 100 micrograms per kilogram of body weight weekly. In another embodiment, the effective dosage amount ranges from about 5 to about 5,000 micrograms per kilogram of body weight over the course of treatment. Notably the dose of 7 µg/kg in 8 total doses used in the Examples was effective to offer substantial protection against a lethal radiation dose when administration began after radiation exposure. Those of skill in the art will appreciate that lower doses may be effective if the radiation exposure is sub-lethal or if the compositions described herein are provided in advance of radiation exposure as a radioprotective agent and not solely to mitigate previous radiation exposure. The effective dosage amounts described herein refer to total amounts administered, that is, if more than one dosage is administered in a period of time, the effective dosage amounts correspond to the total amount administered.

If the composition is administered as more than one dose or as divided doses, the dosage rate and amount may be modified accordingly. For example, the composition may be administered two or more times separated by 4 hours, 6 hours, 8 hours, 12 hours, a day, two days, three days, four days, one week, two weeks, or by three or more weeks, in the Examples, the compositions were given two times per week for a period of four weeks. The compositions may be provided for longer than four weeks, for example for two, three, four months or more.

The cerium oxide nanoparticles may be co-administered with other pharmaceuticals or compositions either in a unitary composition or as two separate compositions. Co-administration of cerium oxide nanoparticles with other compositions may be administered in any order, at the same time or as part of a unitary composition. The two may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

The following examples are meant only to be illustrative and are not meant as limitations on the scope of the invention or of the appended claims. All references cited herein are hereby incorporated by reference in their entireties.

EXAMPLES

Radiation-induced lung injury has traditionally been divided into two phases: the early inflammatory phase and the late fibro-proliferative phase. Histologically, the pneumonitis reaction is characterized by edema, atypia and desquamation of alveolar epithelial cells, intimal proliferation and medial thickening, mononuclear cell infiltrates, giant cell formation, and inflammatory exudates with an absence of polymorphonuclear leukocytes. Hyaline membranes are also seen. Progressive interstitial fibrosis with fibro-obliteration of capillaries, thickened alveolar walls, and lipid-laden, foamy macrophages are seen during the late phase.

Under normal circumstances the cell is able to maintain an adequate homeostasis between the formation of ROS and its removal through particular enzymatic pathways or via antioxidants. However, following radiation exposure to the lung, there is an immediate and continuous increase in chronic oxidative stress that leads to vascular dysfunction, tissue hypoxia, and inflammation and fibro-proliferation. Therefore, we hypothesized suppressing chronic oxidative stress may remove the primary stimulant facilitating the pathogenesis of radiation-induced injury.

We previously characterized the pulmonary dose-response and pathology of injury among six of the most common murine strains utilized as models of radiation-induced lung injury. See Jackson, Vujaskovic, and Down, Revisiting strain-related differences in radiation sensitivity of the mouse lung: recognizing and avoiding the confounding effects of pleural effusions. *Radial Res* 2010, 173, (1), 10-20 and Jackson, Vujaskovic, and Down, A Further Comparison of Pathologies after Thoracic Irradiation among Different Mouse Strains: Finding the Best Preclinical Model for Evaluating Therapies Directed Against Radiation-Induced Lung Damage. *Radial Res* 2011, both of which are incorporated herein by reference in their entireties. The dose-response relationship for lethal pneumonitis in CBA/J mice has been characterized using a single radiation dose of 11.75-14.75 Gy to the whole thorax. Mortality in the CBA/J strain, strongly correlates with increased lung weight, an indicator of edema and congestion, and elevated breathing rates, as marker for functional damage.

We evaluated whether CNP could mitigate lung injury in female CBA/J mice when delivered starting two hours after whole thorax irradiation with a single dose of 15 Gy (LD90/160) of 320 kV x-rays (Dose rate: 0.69 Gy/min, HVL≈2.00 mm Al, 75 cm SSD). Two different formulations of cerium oxide nanoparticles, CNP-18 (Cerium oxide nanoparticles prepared in water; CNP-DW) and CNP-ME (a microemulsion of CNP; CNP-300) were analyzed. See, for example, U.S. Pat. Nos. 7,347,987 and 7,727,559 or U.S. patent application Ser. No. 12/874,398 and Karakoti et al. Nanoceria as Antioxidant: Synthesis and Biomedical Applications JOM (2008) 60:33-37 for methods of preparing cerium oxide nanoparticles, each of which is incorporated herein by reference in its entirety.

Briefly, cerium oxide nanoparticles were prepared using a wet chemical synthesis. A stoichiometric amount of cerium nitrate hexahydrate (99.999%) was dissolved in deionized writer (18.2 MΩ) by constant slow stirring for 10 minutes. The solution is then preferably filtered using a pre-rinsed 20 nm filter paper (ANONDISC-47, 0.02 µm) to remove undissolved and unwanted impurities. The filtered solution is then transferred to a standard flask and stirred slowly and the cerium (III) ions are oxidized using a stoichiometric amount of hydrogen peroxide as an oxidizer, added drop wise while continuing to stir, to form cerium oxide nanoparticles. The amount of hydrogen peroxide influences the time required for the self-assembly of nanoparticles during the aging of the solution. In a typical procedure, the molar ratio of Ce to hydrogen peroxide varied from 1:3 to 1:20. The color and the pH of the solution were monitored continuously during the addition of hydrogen peroxide. The pH of the solution drops below 3.0 by addition of the hydrogen peroxide. The solution is stirred until the typical yellow color of the solution gradually changes to a dark yellow. The stirring is stopped at this point and the solution is transferred to a bottle. Slow evolution of oxygen in the form of bubbles should be observed during aging of the solution. The solution is aged for a minimum of 15 days and it changes color from dark yellow to dark orange and then to light yellow (or colorless). During the aging process the oxidation state of the nanoceria undergoes a dynamic reversibility and changes from predominately $Ce^{4+}$ to $Ce^{3+}$. The aging, allows time dependent oriented agglomeration of nanoparticles in solution with low cerium to hydrogen peroxide ratios. The pH is monitored during the process and increases gradually and is maintained at 1.0-4.5 to keep the nanoparticles in suspension. During aging, the nanoparticle suspension is stored under ambient laboratory conditions in light, at a temperature between 20-30° C. and humidity less than 50%. The CNPs can be stored in the same environment after the aging process and may be dialyzed against deionized water prior to use to eliminate the acid or other impurities. The CNPs can be combined with PEG as described in Karakoti et al. 2009, J Am Chem Soc 131:14144-5, which is incorporated herein by reference in its entirety.

Mice were randomized into groups to receive saline vehicle or one of two formulations of nanoceria, CNP-18 or CNP-ME. Nanoparticles were given by intraperitoneal injection two times per week for four weeks at a high dose of 100 nM (0.007 mg/kg) or a low dose of 10 nM (0.00007 mg/kg). Animals were followed for up to twenty-two weeks for survival (primary parameter). Respiratory function was assessed prior to radiation and every 2 weeks post-radiation using unrestrained whole body plethysmograph. At the time of necropsy, lung tissue was harvested, weighed, and formalin fixed for paraffin embedding. Tissue sections were stained with hematoxylin and eosin to assess histopathologic damage and perivascular and alveolar inflammation.

Figure 2:
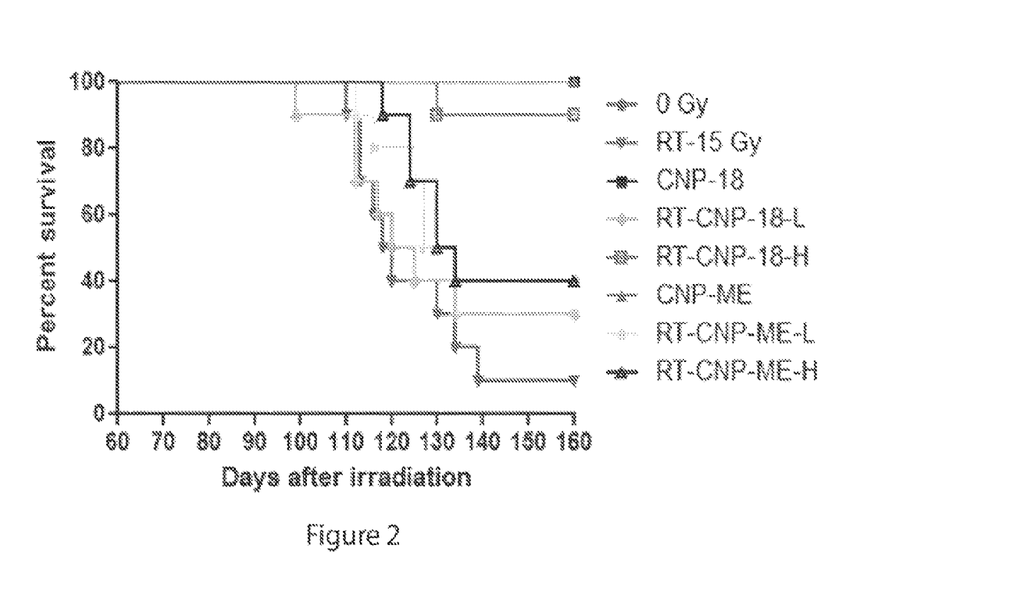
FIG. 2 is a graph showing the percent survival of mice provided the indicated treatments two hours after irradiation over time.
Figure 4:
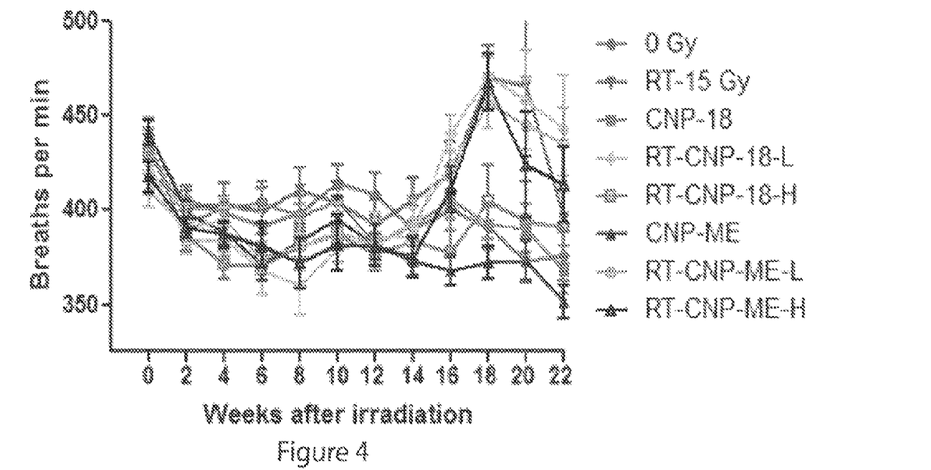
FIG. 4 is a graph showing the change in respiratory rates over time in mice treated with the indicated treatments two hours after irradiation.
Figure 5:
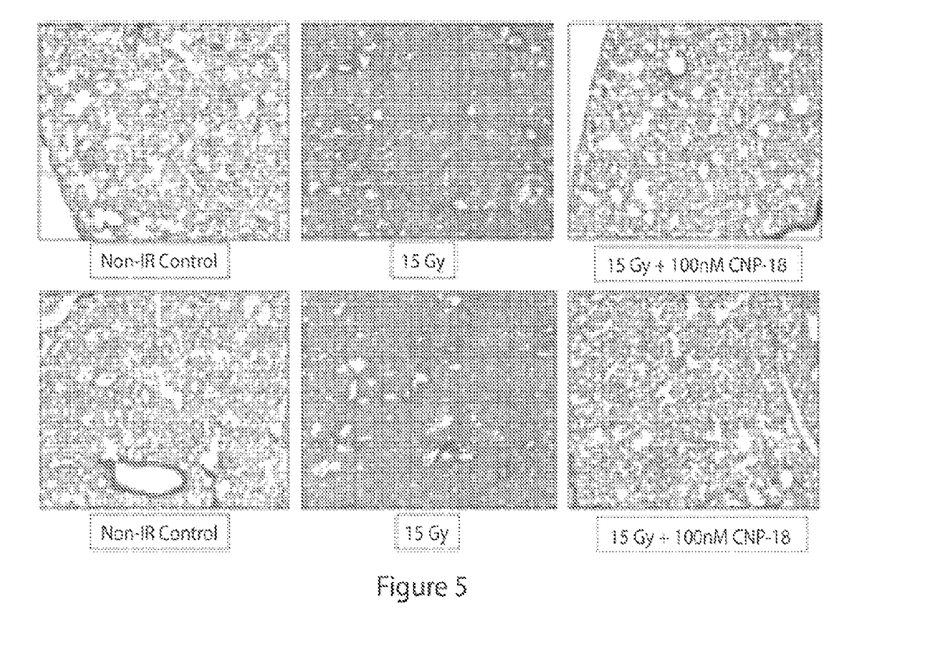
FIG. 5 is a set of photographs showing the histopathology or lung tissue in non-irradiated controls, irradiated controls and in irradiated and treated animals (100 nM CNP-18).

A significant percentage (90%, 9/10) of irradiated animals survived in the 100 nM CNP-18(WB) nanoparticle treated group compared with 10% (1/10) of animals in the RT+saline and 30% (3/10) in RT+10 nM nanoceria-CNP-18(WB) treated groups (FIG. 2). An improvement in multiple respiratory function parameters, including breathing frequency (FIG. 4), enhanced pause (Penh) (FIG. 3), tidal volume (TV), peak inspiratory flow (PIF), peak expiratory flow (PEF) was observed. These results demonstrated a significant mitigating effect on functional injury with 100 nM CNP-18 treatment. Lung histology revealed a significant decrease (p<0.0001) in the structural damage in mice receiving 100 nM CNP-18 nanoparticles (FIG. 5). In addition, significant reduction of in inflammation (p=0.0075) was observed in the 100 nM CNP-18 nanoparticle treated group compared with radiation only control animals (FIG. 5).

We claim:

1. A method of mitigating the effects of radiation exposure in a subject comprising administering a therapeutically effective amount of a composition comprising cerium oxide nanoparticles to the subject, wherein greater than 50% of the cerium in the cerium oxide nanoparticles is in the 3+ oxidation state.

2. The method of claim 1, wherein the composition is administered at the same time as the radiation exposure.

3. The method of claim 1, wherein the composition is administered after the radiation exposure of the subject.

4. The method of claim 3, wherein the composition is administered between 1 hour and 24 hours after the radiation exposure.

5. The method of claim 3, wherein the composition is administered between 1 day and 1 week after the radiation exposure.

6. The method of claim 1, wherein the composition is administered daily, every other day, twice a week, weekly or bimonthly for a period of at least one month.

7. The method of claim 1, wherein the cerium oxide nanoparticles are administered at a dosage of between about 0.00005 mg/kg and about 0.5 mg/kg.

8. The method of claim 7, wherein the dosage is between about 0.005 mg/kg and about 0.05 mg/kg.

9. The method of claim 1, wherein the composition comprises between about 10 nM and 10 µM cerium oxide nanoparticles.

10. The method of claim 9, wherein the composition comprises between about 100 nM and 1 µM cerium oxide nanoparticles.

11. The method of claim 1, wherein the cerium oxide nanoparticles are between 1 nm and 20 nm.

12. The method of claim 1, wherein greater than 80% of the cerium in the cerium oxide nanoparticles is in the 3+ oxidation state.

13. The method of claim 1, wherein the composition was made by dissolving cerium nitrate hexahydrate in water followed by addition of hydrogen peroxide.

14. The method of claim 1, wherein the composition further comprises polyethylene glycol.

15. The method of claim 1, wherein the composition is administered by injection or via an osmotic pump.

16. The method of claim 15, wherein the injection route is selected from intraperitoneal, parenteral, intravenous, intramuscular, subcutaneous, intrathecal, transcutaneous.

17. The method of claim 1, wherein the lungs of the subject are exposed to radiation and treated with cerium oxide nanoparticles, and wherein mitigation of radiation damage includes increased survival, reduced morbidity, decreased lung damage or increased lung function.

18. The method of claim 17, wherein the reduction in morbidity may be monitored by monitoring respiratory function of the subject.

19. The method of claim 1, wherein the composition increases survival of a subject after exposure to radiation by at least 30%.

20. The method of claim 1, wherein the composition is administered before radiation exposure as a radioprotective agent.

* * * * *